United States Patent
Sinelnikov

(10) Patent No.: US 11,832,843 B2
(45) Date of Patent: Dec. 5, 2023

(54) ULTRASONIC SURGICAL INSTRUMENT, ASSOCIATED SURGICAL METHOD AND RELATED MANUFACTURING METHOD

(71) Applicant: MISONIX, INCORPORATED, Farmingdale, NY (US)

(72) Inventor: Yegor Sinelnikov, Port Jefferson, NY (US)

(73) Assignee: MISONIX, LLC, Farmingdale, NY (US)

( * ) Notice: Subject to any disclaimer, the term of this patent is extended or adjusted under 35 U.S.C. 154(b) by 1261 days.

(21) Appl. No.: 16/392,244

(22) Filed: Apr. 23, 2019

(65) Prior Publication Data
US 2019/0247078 A1    Aug. 15, 2019

Related U.S. Application Data

(62) Division of application No. 13/307,691, filed on Nov. 30, 2011, now Pat. No. 10,470,788.
(Continued)

(51) Int. Cl.
*A61B 17/32*    (2006.01)
*A61B 17/00*    (2006.01)

(52) U.S. Cl.
CPC ............ *A61B 17/320068* (2013.01); *A61B 2017/00526* (2013.01); *A61B 2017/00725* (2013.01);
(Continued)

(58) Field of Classification Search
CPC .. A61B 17/320068; A61B 2017/00526; A61B 2017/00725; A61B 2017/320072;
(Continued)

(56) References Cited

U.S. PATENT DOCUMENTS

| 5,989,275 A | 11/1999 | Estabrook et al. ........... 606/169 |
| 6,051,010 A | 4/2000 | DiMatteo et al. ............ 606/169 |

(Continued)

FOREIGN PATENT DOCUMENTS

| EP | 1871478 A2 | 1/2008 |
| WO | WO 00/62688 A1 | 10/2000 |

OTHER PUBLICATIONS

Anderson BE, Griffa M, Larmat C, Ulrich TJ, and Johnson PA. Time reversal. Acoustics Today 2008, 4, 1: 5-11.
(Continued)

*Primary Examiner* — Sarang Afzali
*Assistant Examiner* — Darrell C Ford
(74) *Attorney, Agent, or Firm* — R. Neil Sudol; Henry D. Coleman

(57) ABSTRACT

An ultrasonic therapeutic apparatus includes a handle, a horn or concentrator section terminating in an operative tip, and a transducer assembly set disposed in the handle and operatively engaged with the horn or concentrator section for generating ultrasonic mechanical vibrations therein to vibrate the operative tip during contact thereof with target tissue at a surgical site in a patient. An electrical waveform generator is operatively connected to the transducer assembly for energizing the transducer assembly set with one or more predetermined time reversal ultrasonic waveforms that, upon being applied to the transducer assembly set, result in respective predetermined patterns of motion of the operative tip.

8 Claims, 4 Drawing Sheets

Related U.S. Application Data

(60) Provisional application No. 61/459,121, filed on Dec. 7, 2010.

(52) U.S. Cl.
CPC .............. *A61B 2017/320072* (2013.01); *A61B 2017/320098* (2017.08); *Y10T 29/49002* (2015.01)

(58) Field of Classification Search
CPC ... A61B 2017/320098; Y10T 29/49002; Y10T 29/49005
USPC ............................................ 29/594; 310/311
See application file for complete search history.

(56) References Cited

U.S. PATENT DOCUMENTS

| | | | |
|---|---|---|---|
| 6,278,218 B1 | 8/2001 | Madan et al. ................ 310/312 |
| 6,283,981 B1 | 9/2001 | Beaupre .......... A61B 17/320068 | 606/169 |
| 6,443,969 B1 | 9/2002 | Novak et al. ................. 606/169 |
| 6,561,983 B2 | 5/2003 | Cronin et al. ................. 600/461 |
| 7,476,233 B1* | 1/2009 | Wiener .......... A61B 17/320068 | 606/169 |
| 11,660,088 B2* | 5/2023 | Cohen .............. A61B 17/06166 | 606/228 |
| 2002/0103438 A1 | 8/2002 | Cronin et al. ................. 600/459 |
| 2004/0176717 A1 | 9/2004 | Honda |
| 2005/0261611 A1* | 11/2005 | Makin .................... A61B 5/053 | 601/2 |
| 2006/0241523 A1 | 10/2006 | Sinelnikov |
| 2007/0016235 A1 | 1/2007 | Tanaka et al. ................. 606/169 |
| 2007/0197954 A1* | 8/2007 | Keenan .................. A61B 8/481 | 604/20 |
| 2008/0234709 A1 | 9/2008 | Houser ........................ 606/169 |
| 2008/0243106 A1 | 10/2008 | Cos et al. ........................ 606/1 |
| 2008/0255451 A1 | 10/2008 | Cohen et al. ................. 600/443 |
| 2009/0030438 A1 | 1/2009 | Stulen ........................ 606/169 |
| 2009/0216128 A1 | 8/2009 | Sarvazyan |
| 2009/0218128 A1 | 8/2009 | Sarvazyan .................... 600/459 |
| 2009/0287083 A1 | 11/2009 | Kushculey ............... A61N 7/02 | 600/449 |
| 2010/0094321 A1 | 4/2010 | Akahoshi et al. ............ 606/169 |
| 2014/0357982 A1* | 12/2014 | Malul .................... A61C 3/025 | 606/167 |
| 2023/0079043 A1* | 3/2023 | Genovese ........ A61B 17/22012 |
| 2023/0181207 A1* | 6/2023 | Kingsley .............. A61B 17/285 | 606/167 |

OTHER PUBLICATIONS

Derode A, Tourin A, Fink M. Time reversal versus phase conjugation in a multiple scattering environment. Ultrasonics 2002, 40 (1-8): 275-280.
Fink M, Time-reversal acoustics, Journal of Physics. 2008; 118, 1-28.
Fink M. Time reversed acoustic, Physics Today, 1997; 3, 34-9.
Sutin A, L11313EY B, Kurtenoks Nonlinear detection of land mines using Detection and Remediation Technologies Thomas Broach, Russell S Harmon, pp. 398-409.
Sutin A and Johnson P, Nonlinear elastic wave NDE II: Nonlinear wave modulation spectroscopy and nonlinear time reversed acoustics. In: Review of Quantitative Nondestructive Evaluation, ed. DO Thompson and De Chimenti, AIP, New York, 2005; 24, pp. 385-392.
Sutin A and Sarvazyan A. Spatial and temporal concentrating of ultrasound energy in complex systems by single transmitter using time reversal principles. In: Proceedings of World Congress on Ultrasonics Sep. 7-10, 2003; Paris, pp. 863-866.
Sutin AM, Sinelnikov YD, 2010, Time Reversal Acoustic Approach for Dion Lethal Swimmer Deterrent. Proceedings of the Waterside Security Conference, Marina di Carrara, Italy, November.
Sijtin AM and Sinelnikov YD, 2010, Time Reversal Acoustic Approach for Non Lethal Swimmer Deterrent, J. Acoust. Soc. Am. vol. 128, Issue 4, pp. 2336-2336, lay-language paper: http://www.aeoustics.org/press/16th/sutin.htm.
Quieffin N, Catheline S, Ing R K, Fink M. Real-time focusing using an ultrasonic one channel time-reversal mirror coupled to a solid cavity. J Acoust Soc Am 2004; 115 (5), 1955-60.
Sinelnikov YD, Verdernnikov AV, Sutin AY, Sarvazyan AP, 2010, Time Reversal Acoustic Focusing with a catheter balloon. Ultrasound in Med. & Biol., vol. 36, No. I, pp. 86-94, PMID: 19900754.
Sinelnikov YD, Fjield T, Sapozhnikov OA, 2009, The mechanism of lesion formation by ultrasound ablation catheter for treatment of Atrial Fibrillation. Acoustical Physics vol. 55, 4, 1-12.

\* cited by examiner

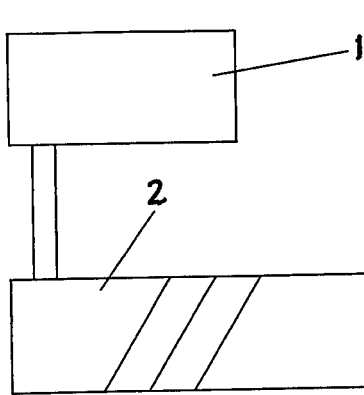
PRIOR ART
FIG. 1
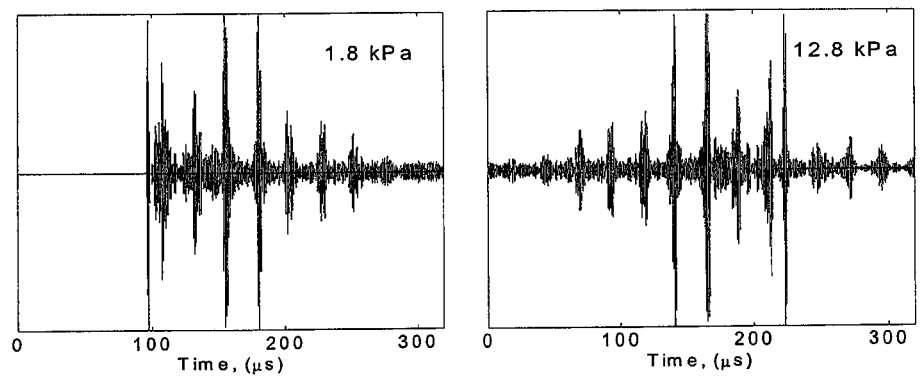
FIG. 2A
FIG. 2B
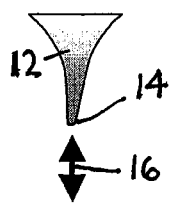
FIG. 3A
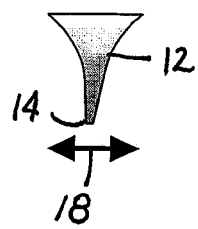
FIG. 3B

SFHS

ULTRASONIC SURGICAL INSTRUMENT, ASSOCIATED SURGICAL METHOD AND RELATED MANUFACTURING METHOD

CROSS-REFERENCE TO RELATED APPLICATIONS

This application is a division of application Ser. No. 13/307,691 filed Nov. 30, 2011, now U.S. Pat. No. 10,470,788 issued Nov. 12, 2019. This application also claims the benefit of U.S. Provisional Patent Application No. 61/459,121 filed Dec. 7, 2010.

BACKGROUND OF THE INVENTION

This invention related to ultrasonic surgical tools and method and also relates to associated manufacturing techniques.

Ultrasonic cutting is widely used in industrial and food processing applications to produce a clean and accurate cut. However, it is still at the doorsteps of worldwide acceptance as a tool in surgical applications, mainly due to the difficulties with deliverability to complex locations and to the high temperatures that can be generated at the cut site.

Ultrasonic bone cutting devices inherit their operating principle from industrial ultrasound cutting devices. The principal schematic of such device is shown in FIG. 1. In response to a signal from a waveform generator 1, an electromechanical transducer 2 produces an ultrasonic standing wave in a horn or concentrator 3, ultrasonically vibrating a tip 3a to grind off sample material from a substrate 6 and to remove the ground material by a flowing abrasive mixture 4, where the substrate 6 is mounted to a ballast or anchor 8 via a compression spring 7. A similar process is used in ultrasound bone or tissue dissection surgery. However, ultrasound dissection of bones operates in a regime of unfavorable conditions.

Bone belongs to a third group of material classification (Kanevski, Acoust Phys. 7, 1-3, 1961) in which the resistance to shear is less than resistance to breakage: $t_p = \tau_p/\sigma_p < 1$, and plastic deformation dominates. In industrial ultrasound, cutting the third group materials is believed to be inefficient. In the materials of the first and second groups: $t_p > 0.5$, and the speed of cutting, $v_{cut}$, is proportional to a product of square of amplitude of vibration, A, and applied pressure, P: $v_{cut} \sim A^2 P$. In the third group: $v_{cut} \sim A\sqrt{P}$. Thus, in bone the speed of cutting cannot be substantially improved by having larger amplitude of vibration or applied pressure. Instead, the literature (e.g. L. D. Rosenberg, Physics and Technique of High Power Ultrasound, Volume 3, Chapter 2, USSR, Moscow, 1970) suggests that the design of the bone cutting ultrasound tip is important, implying that the pattern of tip vibration has also a defining critical effect on the bone cutting process efficiency and speed.

OBJECTS OF THE INVENTION

It is an object of the present invention to provide an improved ultrasonic surgical instrument.

Another object of the present invention is to provide an ultrasonic surgical instrument that is specially adapted to operating at a surgical site that is not accessible by instruments with entirely straight shafts and thus requires a non-linear, curved and asymmetric shaft.

A further object of the present invention is to provide an ultrasonic surgical instrument that has reduced heat output and is accordingly safer for surgical intervention than conventional ultrasonic instruments.

Yet another object of the present invention is to provide an ultrasonic surgical instrument where the operative tip is capable of complex motions. More particularly, the invention contemplates a surgical instrument wherein the operative tip is capable of transverse or shear-type motion as well as longitudinal or compressive-wave motion.

It is yet a further object of the present invention to provide a method of manufacturing such a surgical instrument.

It is an additional object of the present invention to provide an associated surgical method.

These and other objects of the present invention will be apparent from the descriptions and drawings herein. Although all of the objects of the invention are achieved by one or more embodiments of the invention, there is not necessarily any single embodiment that achieves all of the objects of the invention.

SUMMARY OF THE INVENTION

The present invention is based in part on the recognition that the principles of Time Reversal Acoustics (TRA) may be utilized in designing and using an ultrasonic surgical cutting instrument.

Accordingly, the present invention aims in part to provide an ultrasonic surgical instrument where the operative tip is capable of complex motions. More particularly, the invention contemplates a surgical instrument wherein the operative tip is capable of transverse or shear-type motion as well as longitudinal or compressive-wave motion. Preferably, the operative tip of the instrument is capable of achieving a set of substantially different complex motions by controlling the spectral and temporal content of the electrical driving signal applied to piezo-transducers wherein that signal is based on the principles of time invariance.

A method for manufacturing a medical instrument comprises, in accordance with the present invention, (a) fabricating an ultrasonic horn or concentrator having a shape and size configured for a selected type of surgical procedure, (b) operatively connecting an upstream or input portion of the horn or concentrator to an ultrasonic transducer assembly, and (c) energizing the transducer assembly to generate at an input or upstream end of the horn or concentrator an ultrasonic calibration vibration having a desired motion pattern and desired frequency and amplitude characteristics. The manufacturing method further comprises (d) automatically tracking movement of an operative tip of the horn or concentrator upon generation of the calibration vibration at the input or upstream end of the horn or concentrator, (e) automatically recording at least one signal encoding the tracked movement, (f) processing the recorded signal to generate a time reversal waveform, and (g) storing the time reversal waveform in a storage medium. The storage medium is typically a solid-state memory device that is included, for instance, with a microprocessor, in the control unit or waveform generator assembly of an ultrasonic surgical instrument.

The desired motion pattern applied to the upstream end of the horn or concentrator is a pattern to be eventually executed by the operative tip of an ultrasonic surgical instrument having a horn or concentrator section of the same geometrical configuration as the fabricated horn or concentrator receiving the calibration vibration.

This manufacturing process is directed to determining a signal (the time reversal waveform) that is to be applied to a transducer assembly of a surgical instrument during a surgical procedure to cause the operative tip of the surgical instrument to execute the desired motion pattern. As indicated below, this motion pattern may have characteristics that up until this time have been avoided in ultrasonic surgical instruments.

Pursuant to another feature of the present manufacturing method, the horn or concentrator is a test or calibration device and the transducer assembly is a test or calibration assembly, both parts of a test or calibration apparatus. In that case, the manufacturing method further comprises packaging the storage medium with an ultrasonic medical instrument for commercial or retail sale. The commercial or retail instrument includes a handle, a horn or concentrator section terminating in an operative tip, a transducer arrangement disposed in the handle and operatively engaged with the horn or concentrator section for generating ultrasonic mechanical vibrations therein to vibrate the operative tip during contact thereof with target tissue at a surgical site in a patient, and an electrical waveform generator operatively connected to the transducer arrangement for energizing same with an electrical waveform, the waveform generator including the storage medium storing the time reversal waveform. The horn or concentrator section of the packaged instrument is operatively identical to the test or calibration device, while the transducer arrangement being operatively identical to the test or calibration assembly.

Alternatively, the storage medium may be packaged with the test or calibration apparatus and sold commercially for eventual use in a surgical procedure. This methodology contemplates that every instrument is individually calibrated during manufacture and loaded with one or more individually or respectively determined time reversal waveforms. A commercial or retail instrument pursuant to this methodology naturally includes a handle, the horn or concentrator being connected to the handle, the transducer assembly being disposed in the handle and operatively engaged with the horn or concentrator for generating ultrasonic mechanical vibrations therein to vibrate the operative tip during contact thereof with target tissue at a surgical site in a patient. The instrument further includes an electrical waveform generator operatively connectable to the transducer assembly for energizing the same with an electrical waveform, the waveform generator including the storage medium storing the time reversal waveform.

The ultrasonic calibration vibration may be a short harmonic or frequency sweep pulse, the movement of the tip being a long reverberation signal. However, the calibration vibration and tip movement may be more complex to accommodate specific surgical procedures.

The processing of the recorded signal includes time reversing the recorded signal and normalizing the time-reversed signal. In generating the time reversal waveform in an actual instrument in a surgical procedure, the signal is preferably amplified.

The present invention enables the manufacturing of a surgical instrument designed in part to enable tip movement that includes a shear component. Accordingly, the transducer assembly used in the manufacturing method is so configured relative to the horn or concentrator to produce, in a proximal end portion of the horn or concentrator, ultrasonic vibrations having a transverse or shear component. The ultrasonic calibration vibration may then include a transverse or shear component.

The present invention provides for the manufacture of a functional surgical instrument having a horn or concentrator section that is asymmetric about a longitudinal axis of the upstream or input portion of the horn or concentrator section. For instance, a distal end portion of the horn or concentrator section may be disposed completely to one side of the proximally defined longitudinal axis. Tracking the movement of the operative tip of the horn or concentrator may be implemented by any suitable technique including, but not limited to, operating at least one laser vibrometer. The vibrometer is preferably capable of tracking horn tip movement in three dimensions, namely, a longitudinal dimension and two transverse dimensions or shear directions. In addition, the vibrometer is capable of assessing the direction and magnitude of surface vibration in the critical regions, where for the procedural reasons said vibrations need to be reduced or maximized.

A time reversal acoustic or ultrasonic waveform determined in a manufacturing method pursuant to the present invention is incorporated into a surgical instrument and enables or facilitates effective operation of the instrument in a surgical setting. An ultrasonic therapeutic apparatus in accordance with the present invention comprises a handpiece including a handle, a horn or concentrator section terminating in an operative tip, and a transducer assembly disposed in the handle and operatively engaged with the horn or concentrator section for generating ultrasonic mechanical vibrations therein to vibrate the operative tip during contact thereof with target tissue at a surgical site in a patient. The apparatus further comprises an electrical waveform generator operatively connected to the transducer assembly for energizing the transducer assembly with an electrical waveform. The waveform generator is programmed to produce a predetermined time reversal acoustic or ultrasonic waveform that, upon being applied to the transducer assembly, results in a predetermined pattern of motion of the operative tip. In many surgical instruments in accordance with the present invention the desired pattern of motion of the operative tip bears little discernible similarity to the time reversal acoustic waveform generated at the input end of the instrument. The tip movement results from the complex wave interactions in the horn or concentrator section, including multiple reflections and wave superposition.

Pursuant to a feature of the present invention, the waveform generator of the surgical instrument is programmed to produce a plurality of predetermined time reversal acoustic signal waveforms that, upon being separately or simultaneously applied to the transducer assembly, result in respective predetermined motions of the operative tip. The waveform generator may be programmed to reproduce the various stored time reversal acoustic or ultrasonic waveforms alternately, in a multiplexed mode of operation. The waveform generator may be configured to automatically deliver the different time reversal acoustic or ultrasonic waveforms in a multiplexed or alternating sequence. In that case, upon a surgeon's manual activation of a switch or selector input element operatively connected to the waveform generator, a preprogrammed sequence of time reversal acoustic or ultrasonic waveforms is generated at the input end of the horn or concentrator section of the instrument's handpiece. Alternatively or additionally, the surgical instrument may be configured to enable a surgeon to select the different time reversal acoustic or ultrasonic waveforms one by one pursuant to exigent requirements. A further option may be to reproduce more than one of the stored time reversal acoustic or ultrasonic waveforms simultaneously to generate a composite complex movement of the surgical instrument's operative tip.

As indicated above, one or more of the time reversal acoustic or ultrasonic waveforms may include a transverse, shear-action motion component. Concomitantly, the predetermined motion of the operative tip resulting from the infeed time reversal acoustic or ultrasonic waveforms may include a transverse or shear-action motion component. Of course, the predetermined motion of the operative tip may additionally or alternatively include a longitudinal compression wave component, depending on the characteristics of the time reversal acoustic or ultrasonic waveforms.

The horn or concentrator section of the surgical instrument may have an asymmetric shape where the distal end portion of the horn or concentrator section extends to only one side of a longitudinal axis defined by the geometry of the proximal end of the concentrator section.

In order to produce transverse or shear waves, the transducer assembly may include at least one compression-wave transducer having a transmission axis oriented at an angle relative to a longitudinal axis of the input or upstream end of the horn or concentrator section. Where the angle of transducer orientation is less than 90° (an acute angle) the transducer assembly will also inevitably produce a longitudinal compression wave component when the off-angle transducer is activated.

An associated ultrasonic therapeutic method comprises, in accordance with the present invention, providing an ultrasonic surgical instrument which includes a handle, a horn or concentrator section terminating in an operative tip, a transducer assembly disposed in the handle and operatively engaged with the horn or concentrator section, and an electrical waveform generator operatively connected to the transducer assembly. The method also comprises manipulating the handle, thereby placing the operative tip into contact with target organic tissues at a preselected surgical site within a patient, and during that contact operating the waveform generator to apply a predetermined time reversal acoustic waveform to the transducer assembly and thereby concomitantly generate corresponding ultrasonic mechanical vibrations in the horn or concentrator section to result in a predetermined pattern of vibration of the operative tip.

In an associated ultrasonic therapeutic method in accordance with the present invention, the waveform generator may be operated to alternately or simultaneously produce multiple predetermined time reversal acoustic waveforms that, upon being separately applied to the transducer assembly, result in respective predetermined patterns of vibration of the operative tip. The production of the multiple predetermined time reversal acoustic waveforms may be automatically implemented or, alternatively, executed in accordance with manually input selections. The multiple predetermined time reversal acoustic waveforms may include one or more transverse, shear-action motion components and additionally or alternatively a longitudinal compression wave component.

The method of the present invention is of particular use where the horn or concentrator section has an asymmetric or complex shape, for instance, with the distal end portion of the horn or concentrator section extending to only one side of a longitudinal axis of the handle and a proximal portion of the horn. The predetermined pattern of vibration of the operative tip differs from the time reversal acoustic waveform, owing to the geometrical configuration of the horn or concentrator section. The asymmetric or complex shape or the horn section may be determined in part by anatomical restrictions inherent in a particular kind of surgical procedure. The horn is designed to accommodate or comply with those anatomical restrictions.

BRIEF DESCRIPTION OF THE DRAWINGS

FIG. 1 is partially a block diagram and partially a schematic representation of an industrial ultrasonic cutting device.

FIG. 2A is a graph showing input and output waveforms during a calibration phase in the manufacture of an ultrasonic instrument.

FIG. 2B is a similar graph showing a time reversed input waveform and a desired output vibration of an ultrasonic instrument, where the time reversed input waveform is determined during the calibration phase of FIG. 2A.

FIG. 3A is a schematic representation of a horn or concentrator section, including an operative tip or end effector, of an ultrasonic surgical instrument, showing a first type of movement of the tip enabled by the present invention.

FIG. 3B is a schematic representation of the horn or concentrator section of FIG. 3A, including the operative tip or end effector, showing a second type of movement of the tip enabled by the present invention.

DETAILED DESCRIPTION

Figure 3C:
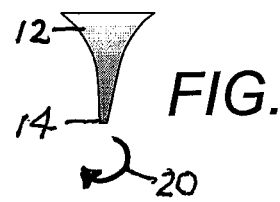
FIG. 3C is a schematic representation of the horn or concentrator section of FIGS. 3A and 3B, including the operative tip or end effector, showing a third type of movement of the tip enabled by the present invention.

Time reversal energy concentration systems (Fink, Time reversal acoustics. Scientific American, 1999, 91-97), based on the TRA principles, are capable of concentrating ultrasound to a chosen location in a heterogeneous medium. Time reversal energy concentration is very efficient in structures with numerous interfaces and boundaries made of high quality materials that do not attenuate acoustic signals. Multiple reflections from internal boundaries and internal structures are taken into account by the ability of TRA system ability to concentrate energy. Excellent focusing ability of TRA has been utilized in various biomedical applications (Sinelnikov et al, 2009, Fink 2008, Quieffin et al., 2004; Sutin and Sarvazyan, 2003), geophysics (Anderson et al, 2008), nondestructive testing (Sutin and Johnson, 2005), and land mine detection (Sutin et al. 2006). TRA focusing systems described in the literature are based on the use of specially constructed solid reverberators with several or single transmitters. It is deemed feasible to implement TRA focusing using a single transducer and reverberator and seek to achieve effective vibration enhancement at a tip of a surgical cutting blade.

Pursuant to the present invention, TRA energy concentration is achieved in a sequence of three steps. First, a short harmonic pulse (FIG. 2A, gray line) is applied to the transmitting transducers, which radiates corresponding acoustic signals into the concentrator. Second, a long reverberation signal (FIG. 2A, black line) resulting from the multiple bouncing of ultrasonic waves within the concentrator is detected at the tip by a laser vibrometer and recorded. Third, the recorded reverberated signal is time reversed (FIG. 2B, gray line) using a desktop computer, normalized, amplified, and applied back to the same transducer. The signal travels through concentrator, reverberates, and assembles itself in a sharp, high intensity spike of vibration energy at the tip location, where laser vibrometer recording initially took place at the second step. The resultant high-amplitude time-reversed signal is shown in FIG. 2B by black.

In a pilot experiment described elsewhere (Sinelnikov et al. 2010) six fold magnification (from 1.8 to 12.8 kPa as shown on FIG. 2) of the acoustic intensity was achieved with single transducer. Time reversal principles have been demonstrated effective for non-lethal diver deterrent in a shallow waveguide environment of the commercial harbors (Satin and Sinelnikov, 2010).

Moreover, the intensity of the TRA focused signal can be increased by modifying irradiated signal amplitude while preserving the phase, and some research has demonstrated TRA principles can be applied to continuous radiating signals (Derode et al, 2002), like those used in bone cutting devices.

An ultrasonic surgical instrument with a concentrator or horn and a bone scalpel blade provides an outstanding structure for time reversal energy concentration to take place. The present invention recognizes that modification of the operating principle of an ultrasonic bone scalpel and its shape can reduce bone resection times and still provide a surgical safe device. Adding a shear or combination of shear and longitudinal vibrations to motion of an ultrasonic blade tip can substantially increase the bone cutting speed and improve efficiency. An ability to engage the tip of the blade in different mode of vibration becomes important and can be achieved using the principle of time reversal, applied to a long burst of signals as it was recently presented by Y. D. Sinelnikov at a recent meeting of the Acoustical Society of America (October 2009, Generation of long pulses of focused ultrasound by time reversal system, J. Acoust. Soc. Am. 126, 4, 2215).

Figure 3D:
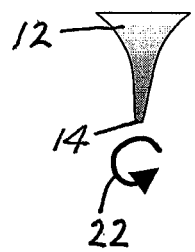
FIG. 3D is a schematic representation of the horn or concentrator section of FIGS. 3A-3C, including the operative tip or end effector, showing a fourth type of movement of the tip enabled by the present invention.
Figure 3E:
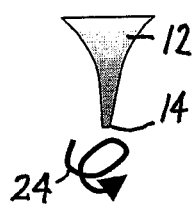
FIG. 3E is a schematic representation of the horn or concentrator section of FIGS. 3A-3E, including the operative tip or end effector, showing a fifth type of movement of the tip enabled by the present invention.

For example, reference being made to FIGS. 3A-3E, the bone cutting speed of a ultrasonic surgical instrument with a horn or concentrator section 12 and an operative tip or blade 14 can be increased by multiplexing different modes, such as a pure longitudinal (standard) mode represented by a double headed arrow 16 in FIG. 3A, a shear mode represented by a double headed arrow 18 in FIG. 3B, and a clockwise or a counter-clockwise rotation mode respectively represented by arcuate arrows 20 and 22 in FIGS. 3C and 3D. In FIG. 3E, a corkscrew arrow 24 represents a composite motion with both longitudinal and shear components.

It is believed that operating the tip 14 of an ultrasonic cutting blade in only a longitudinal mode (FIG. 3A) does not lead to an improved efficiency, because, as mentioned above, bone belongs to the third group, where plastic deformation dominates and high viscosity of bone frame resists efficient single mode breakage of its structure. In this situation, switching between modes of tip vibration either on operator demand or automatically can lead to a higher cutting speed, more efficient material removal, and elimination of the bone frame packing effect, know to arise when high amplitude vibrations are applied in a single direction.

Such changes in the mode of blade tip vibration are achievable using the principle of time reversal (M. Fink, 1992, Time reversal of ultrasonic fields, IEEE Trans. On Ultrason, Ferroelectr, and Freq Control, 39, 5, 555-566). Research in this field has demonstrated that a time reversal principle can be applied to focus long pulses of ultrasound, thus enabling ultrasound focusing in a continuous regime. Initial results were highlighted in a collaborative work of Y. D. Sinelnikov and A. Y. Sutin (J. Acoust. Soc. Am. 126, 4, 2215). A similar procedure can be applied to an acoustic concentrator system like that shown in FIG. 1. Concentrator 3 can be a conical, exponential, or catenoidal horn combined with a constant cross section rod. (Merkulov, L. G. and A. V. Kharitonov, Theory and design of sectional concentrators, Soviet Physics—Acoustics, Vol. 5, 183-190, 1959) Such a sectional concentrator 3 makes it possible to obtain considerably large oscillatory amplitudes and deformations at the operative tip $3a$. At the same time, such a concentrator 3 works as an efficient high-mechanical-quality acoustic resonator, where acoustic energy reverberates multiple times, and multiple resonances are present along with major longitudinal resonance. The latter creates a condition most favorable for performing time reversal and attempting to maximize the tip movement in one or another direction. While exciting concentrator 3 in an oscillatory movement other than longitudinal is conventionally regarded as having negative consequences, it is possible to apply time reversal principle to control these additional resonances and provide an input signal that would produce a desired tip movement, such as shown in FIGS. 3A-3E.

Figure 4A:
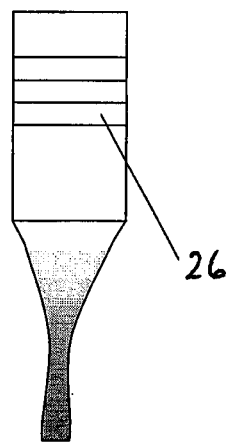
FIG. 4A is a schematic side elevational view of an ultrasonic surgical instrument handpiece, showing a stacked transducer array for generating longitudinal compressive waves in a horn or concentrator section of the instrument.
Figure 4B:
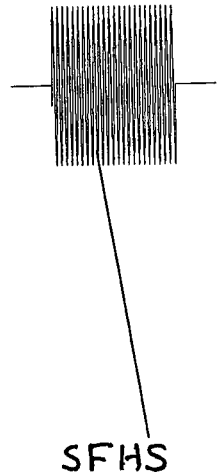
FIG. 4B shows a harmonic activation signal for energizing the transducer array of FIG. 4A.
Figure 4C:
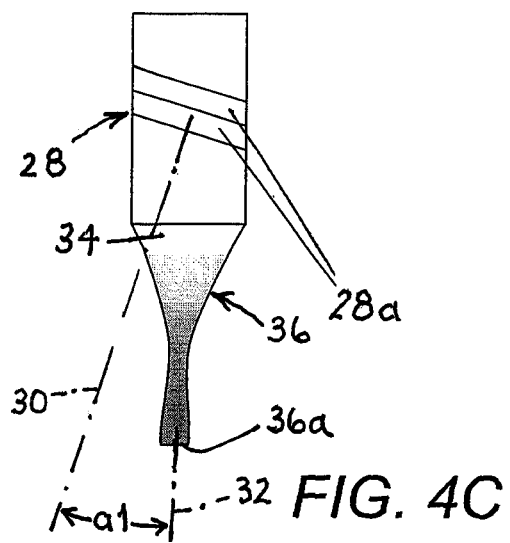
FIG. 4C is a schematic side elevational view of another ultrasonic surgical instrument handpiece, showing an array of obliquely stacked transducers for generating, in a horn or concentrator section of the instrument, a vibratory waveform having both a longitudinal, compressive component and a transverse, shear component.
Figure 4D:
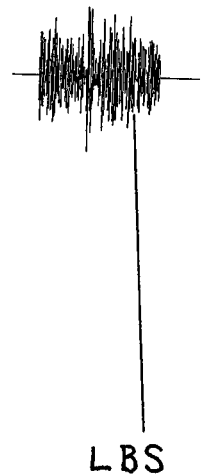
FIG. 4D shows a limited bandwidth quazi-harmonic activation signal for energizing the transducer array of FIG. 4C.

Conventional bone-cutting and similar ultrasonic surgical devices of the prior art are activated in a strictly longitudinal mode of vibration (FIG. 3A), using a sharply tuned single frequency harmonic signal SFHS (FIG. 4B) supplied by a stacked set of powerful planar disc transducers 26, as depicted in FIG. 4A. A predominantly longitudinal mode of vibration is excited in this configuration. In order to generate arbitrary concentrator tip movement, for example, as shown in FIGS. 3B-3E, this structure of transducers 26 or a modified transducer array 28 (FIG. 4C) can be used in combination with a limited bandwidth signal LBS (FIG. 4D) constructed by the time reversal process, thus deviating from the original single frequency harmonic signal and possibly reducing the overall amount of energy required to elicit the blade movement necessary for surgery, which may also lead to an overall reduction of unwanted temperature effects associated with ultrasound surgery.

Transducer array 28 (FIG. 4C) comprises a plurality of compression-wave transducer elements 28a such as piezoelectric disks having a transmission axis 30 oriented at an angle a1 relative to a longitudinal axis 32 of an input or upstream end 34 of a horn or concentrator section 36 having an operative tip 36a. Where the angle of transducer orientation a1 is less than 90° (an acute angle) the transducer assembly 28 will also inevitably produce a longitudinal compression wave component when the off-angle transducer is activated.

Figure 5A:
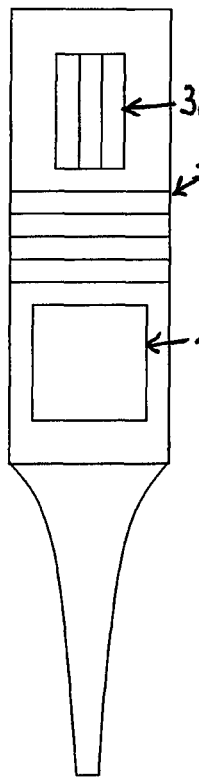
FIG. 5A is a schematic front elevational view of a further ultrasonic surgical instrument handpiece, showing a pair of shear mode transducer arrays and a longitudinal mode transducer array, for excitation by one or more time reversal ultrasonic waveforms, in accordance with the present invention.
Figure 5B:
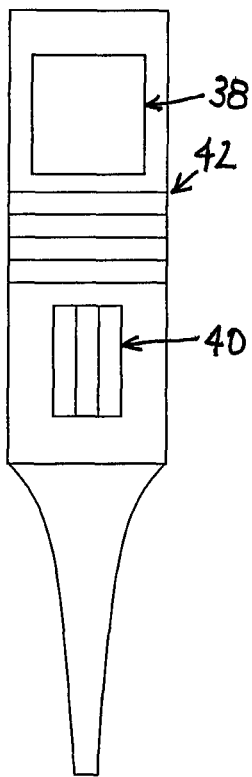
FIG. 5B is a schematic side elevational view of the ultrasonic surgical instrument handpiece of FIG. 5A.
Figure 6A:
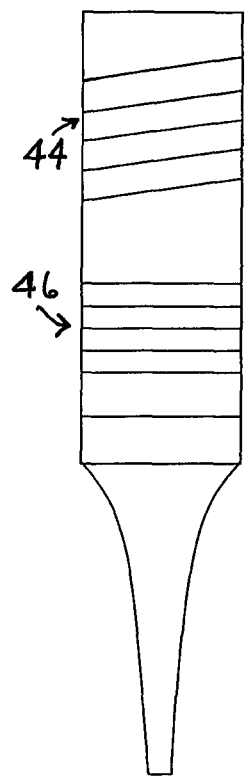
FIG. 6A is a schematic front elevational view of yet another ultrasonic surgical instrument handpiece, showing a pair of obliquely stacked transducer arrays, for excitation by one or more time reversal ultrasonic waveforms, in accordance with the present invention.
Figure 6B:
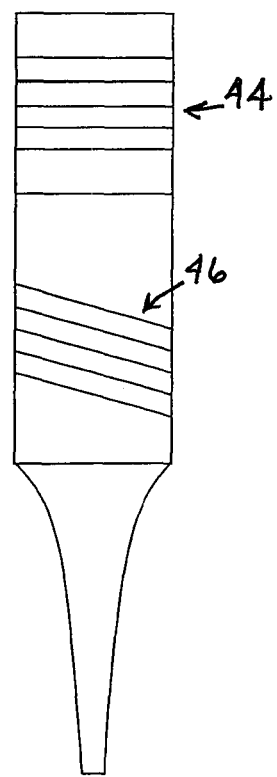
FIG. 6B is a schematic side elevational view of the ultrasonic surgical instrument handpiece of FIG. 6A.

An alternative transducer configuration for activation by time reversal ultrasonic waveforms can incorporate one or more shear mode transducer arrays 38, 40 either alone or together with a longitudinal compressional mode transducer array 42, as shown in FIGS. 5A and 5B. A further alternative transducer configuration depicted in FIGS. 6A and 6B includes a plurality of asymmetrically mounted compressional transducer arrays 44, 46. In use, these modified transducer assemblies (FIG. 4C, FIGS. 5A and 5B, FIGS. 6A and 6B) are activated by time reversal ultrasonic waveforms respectively determined during a time reversal calibration process to produce instrument tip movements of desired patterns and amplitudes.

Transducer arrays 28, 38 and 40, 44 and 46 naturally generate non-longitudinal sectional concentrator resonance vibration modes and, when excited by time reversal ultrasonic waveforms, produce tip movements of desired types for efficient cutting of bone and other kids of tissue. The excitation of multiple resonances creates multiple conversions of compressional waves to shear waves at internal and external interfaces of the concentrators, which further complicates the reverberation passes and decreases the amplitude of longitudinal resonance. However, these multiple conversions and complexities are obviated through the excitation of other resonance modes by using time reversal ultrasonic excitation waveforms, to achieve predictable and desirable tip movement. By activating transducer arrays 28, 38 and 40, 44 and 46 with time reversal waveforms at respective resonance frequencies, the tip 36a of the horn or concentrator section 36 can be controlled to move in different predetermined patterns. Therefore, a continuous quazi-harmonic signal can be constructed as a superposition of desired single resonance waveforms to produce different controllable tip movement. The reduction of overall power and reliance on multiple reverberation inside the concentrator 36 are also expected to reduce the high temperatures at the tip 36a of the blade that typically are generated at the cut site.

Figure 7:
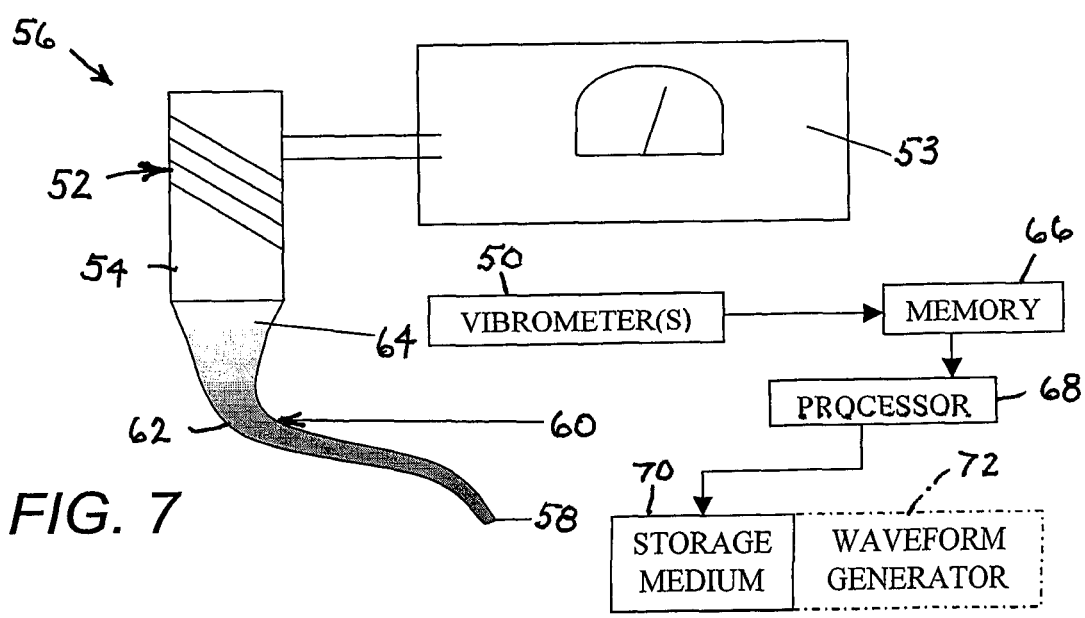
FIG. 7 is a schematic diagram of an ultrasonic surgical system, showing a vibrometer for use in a calibration or manufacturing method in accordance with the present invention.

As depicted in FIG. 7, a method for manufacturing an ultrasonic surgical instrument that produces different tip vibrations may include the use of one or more laser vibrometers 50 or similar optical fast movement monitoring equipment that allows recording of the concentrator tip movement at a sampling rate at least two times the highest resonance frequency in a selected concentrator resonance frequency set. The desired time reversal ultrasonic waveform is constructed during a calibration process by applying a short pulse to an activation transducer set or assembly 52 disposed, e.g., inside a handle 54 of an ultrasonic instrument 46 and recording an impulse response at a tip 58 at various power levels of an activation waveform delivered to transducer assembly 52 by a calibration signal generator 53.

Where the input ultrasonic calibration vibration is a short harmonic pulse, the movement of tip 58 is typically a long reverberation signal. However, the calibration vibration and tip movement may be more complex to accommodate specific surgical procedures.

Repetitive application of a time reversed impulse response convoluted with a harmonic waveform of a predefined content results in tip vibration in a desired mode. With linear superposition of vibration modes, a desired two or three dimensional tip movement is decomposed to construct input waveforms that result in only longitudinal, shear, or combination of such modes. Thus this method enables control of tip movement and improves bone cutting by switching between vibration patterns. Moreover, this method enables the use of substantially curved tip 58 and on-demand shaped concentrators 60 for specialized procedures, where access to the delivery site is critical, as shown in FIG. 7.

In curved concentrators such as horn or concentrator section 60, depending on concentrator geometry and the respective surgical site and access path, there may arise a constraint to minimize vibration at certain regions 62 of the concentrator, while still achieving the desired pattern of vibration of the operative tip 58. In this case the input waveform can be constructed by solving the non-linear regression problem or by filtering signals that would otherwise lead to the magnification of vibration in the control regions 62. If linear conditions are to hold at high power, the desired waveform may be constructed by simple time domain subtraction of the control region signals from the signal that would produce maximum desired movement of tip 58. The ability to enhance the desired vibration of tip 58, while minimizing vibration in control regions 62, will in many cases provide a solid design constraint on the shape of a particular concentrator 60. With the help of a relatively simple computer simulation, the shape of curved concentrator 60 can be fine tuned before production in order to achieve desired site access goals and enable most efficient movement of tip 58 at high power, while minimizing unwanted vibration in control regions 62 of concentrator 60. Such curved designs 60 may be suitable for a broad range of medical applications from cranial, spinal cord and orthopedic surgery to dentistry and facial reconstruction. Besides osseous bone dissection sculpting removal, practical soft tissue applications include wound cleansing and debridement of ulcers, tumor removal and tissue debulking, liposuction and body contouring. Potential applications of a TRUST (Time Reversal Ultrasonic Surgical Tip) system are summarized in Table 1.

TABLE 1

Potential Applications of TRUST system

| | | | |
|---|---|---|---|
| Advanced Wound Care | Wound Cleansing & Debridement | Soft to Hard | Ulcers Infections to Eschar Necrotic Bone |
| Orthopedics Neurosurgery | Bone Dissection Bone Sculpting & Removal | Osseous | Small Bone & Spinal |
| Neurosurgery General Surgery | Tumor Removal Tissue Debulking Bone Sculpting & Removal | Soft to Hard | Liquid, Gelatinous Tumors to Fibrous, Calcified, Osseous |
| Aesthetic Surgery Plastic Surgery | Liposuction & Body Contouring | Soft | Adipose |

In a method for manufacturing a medical instrument 56 in accordance with above-described time reversal principles, one fabricates an ultrasonic horn or concentrator 60 having a shape and size configured for access in a selected type of surgical procedure. An upstream or input portion 64 of the horn or concentrator 50 is connected to an ultrasonic transducer assembly 52 capable of producing sufficient shear mode and longitudinal mode vibrations. Subsequently, one energizes transducer assembly 52 to generate at input or upstream end 64 of horn or concentrator 60 an ultrasonic calibration vibration having a desired motion pattern and desired frequency and amplitude characteristics. The motion pattern and the frequency and amplitude characteristics are those that one desires to occur at the tip 58 of the instrument during a surgical procedure at a target surgical site inside a patient. Consequent movement of operative tip 58 of horn or concentrator 60 is automatically tracked and recorded by means of vibrometer(s) 50. At least one signal encoding the tracked movement is recorded in a memory unit 66. The recorded signal is utilized by a signal processor 68 to generate a time reversal waveform which is normalized and then delivered to a storage medium 70. The storage medium 70 is typically a solid-state memory device that is included, for instance, with a microprocessor, in a control unit or waveform generator assembly 72 of an ultrasonic surgical instrument, which may be instrument 56 or another essentially identical instrument. In generating the time reversal waveform in an actual instrument in a surgical procedure, the signal is preferably amplified prior to being applied to the transducer array.

The time reversal waveform that is entered into storage medium 70 is to be applied to transducer assembly 52 of surgical instrument 56, or of another essentially identical instrument, during a surgical procedure to cause the operative tip 48 of that surgical instrument to execute the desired motion pattern. This motion pattern may have characteristics that up until this time have been avoided in ultrasonic surgical instruments.

Horn or concentrator 60 is typically a test or calibration device while transducer assembly 52 is concomitantly a test or calibration assembly. In that case instrument 56 is a dedicated calibration device for determining a time reversal signal, while storage medium 70 and waveform generator assembly 72 are incorporated into a particular surgical instrument intended for commercial distribution. Then the manufacturing method further comprises packaging storage medium 70 with the commercial ultrasonic medical instrument.

The commercial or retail instrument is to all practical purposes identical to instrument 56 and thus includes ultrasonic transducer assembly 52, handle 54, horn or concentrator section 60 exhibiting one or more temperature-control regions 62 and terminating in operative tip 58. The transducer assembly 52 of the commercial instrument is disposed inside handle 54 and is operatively engaged with horn or concentrator section 60 for generating ultrasonic mechanical vibrations therein to vibrate operative tip 58 during contact thereof with target tissue at a surgical site in a patient. Electrical waveform generator 72 of the commercial or retail instrument is operatively connected to transducer assembly 52 for energizing the same with a time reversal ultrasonic waveform stored in storage medium 70. Medium 70 may be a part of waveform generator 72.

Alternatively, instrument 56 (FIG. 7) may itself be an instrument intended for commercial distribution. Instrument 56 is thus individually calibrated, vibration tested, and loaded with time reversal ultrasonic waveforms for eventual use during one or more surgical procedures.

The above-described procedure enables the manufacturing of a surgical instrument wherein tip movement may include a shear component. Accordingly, transducer assembly 52, as used in the manufacturing method, is so configured relative to horn or concentrator 60 as to produce, in proximal or upstream end portion 64 of the horn or concentrator, ultrasonic vibrations having a transverse or shear component. The ultrasonic calibration vibration may then include a transverse or shear component.

The above-described procedure enables the manufacture and use of a functional surgical instrument having a horn or concentrator section 60 (FIG. 7) that is asymmetric about a longitudinal axis 74 of upstream or input portion 64 of horn or concentrator section 60. A distal end portion 76 of horn or concentrator section 60 may thus be disposed completely to one side of the proximally defined longitudinal axis 74. Tracking the movement of operative tip 58 of horn or concentrator 60 may be implemented by any suitable technique in addition to or alternatively to at least one laser vibrometer 50. Vibrometer(s) 50 is preferably capable of tracking horn tip movement in three dimensions, namely, a longitudinal dimension and two transverse dimensions or shear directions.

A time reversal ultrasonic waveform determined in a manufacturing method as described above is incorporated into a surgical instrument and enables or facilitates effective operation of the instrument in a surgical setting. The surgical instrument may be provided with multiple stored time reversal ultrasonic waveforms each for implementing a predetermined motion of the operative tip.

Accordingly, an ultrasonic therapeutic apparatus comprises a handpiece including a handle 54 (FIG. 7), a horn or concentrator section 60 terminating in an operative tip 58, and a transducer assembly 52 disposed in the handle 54 and operatively engaged with the horn or concentrator section 60 for generating ultrasonic mechanical vibrations therein to vibrate the operative tip 58 during contact thereof with target tissue at a surgical site in a patient. An electrical waveform generator 72 is operatively connected to transducer assembly 52 for energizing the transducer assembly with an electrical waveform. Waveform generator 72 is programmed (via memory 70) to produce one or more predetermined time reversal acoustic or ultrasonic waveforms that, upon being applied to transducer assembly 52, result in respective predetermined patterns of motion of operative tip 58. In many such surgical instruments, the desired pattern of motion of the operative tip bears little discernible similarity to the time reversal acoustic waveform generated at the input end 64 of horn or concentrator section 60. Movement of tip 58 results from the complex wave interactions in horn or concentrator section 60, including multiple reflections and wave superposition.

Again, waveform generator 72 of a surgical instrument manufactured as discussed above may be programmed to produce a plurality of predetermined time reversal ultrasonic waveforms that, upon being separately applied to the transducer assembly 52, result in respective predetermined motions of the operative tip. Waveform generator 72 may be programmed to reproduce the various stored time reversal ultrasonic waveforms alternately, in a multiplexed mode of operation. The operation of waveform generator 72 to reproduce the stored time reversal ultrasonic waveforms may be automatic—so that upon a surgeon's manual activation of a switch or selector input element (not illustrated) operatively connected to waveform generator 72, a preprogrammed sequence of time reversal acoustic or ultrasonic waveforms is generated at input end 64 of horn or concentrator section 60. Alternatively or additionally, the surgical instrument may be adapted to enable a surgeon to select different time reversal acoustic or ultrasonic waveforms one by one pursuant to exigent requirements. A further option is to reproduce two or more of the stored time reversal acoustic or ultrasonic waveforms simultaneously to generate a composite complex movement of the surgical instrument's operative tip 58.

Again, one or more of the stored time reversal acoustic or ultrasonic waveforms typically include a transverse, shear-action motion component. For such waveforms, the respective predetermined motions of operative tip 58 include a transverse or shear-action motion component. It is contemplated that the predetermined motion of operative tip 58 optionally includes a longitudinal compression wave component.

Transducer assembly 52 may take any of the forms disclosed herein with reference to FIGS. 4A, 4C, 5A and 5B, and 6A and 6B. Transducer assembly 52 as depicted in FIG. 7 is similar to transducer array 28 of FIG. 4C. Transducer assembly 52 comprises a plurality of compression-wave transducer elements 78 in the form of piezoelectric disks having a transmission axis 80 oriented at an angle a2 relative to a longitudinal axis 2 of input or upstream end 64 of horn or concentrator section 60. Where the angle of transducer orientation a2 is less than 90° (an acute angle) the transducer assembly 52 will also inevitably produce a longitudinal compression wave component when the off-angle transducer is activated.

In a therapeutic method utilizing an ultrasonic instrument as described hereinabove with reference to FIG. 7, a surgeon manipulates handle 54, thereby placing operative tip 58 into contact with target organic tissues at a preselected surgical site within a patient, and during that contact operates waveform generator 72 to apply one more predetermined time reversal acoustic waveforms to transducer assembly 52, thereby generating corresponding ultrasonic mechanical vibrations in horn or concentrator section 60 to result in one ore more predetermined patterns of vibration of operative tip 58.

As discussed above, waveform generator 72 may be operated to alternately or simultaneously produce multiple predetermined time reversal acoustic waveforms that, upon being separately applied to transducer assembly 52, result in respective predetermined patterns of vibration of operative tip 58. Again, the production of the multiple predetermined time reversal acoustic waveforms may be automatically implemented or, alternatively, executed in accordance with multiple manually input selections. The multiple predetermined time reversal acoustic waveforms may include one or more transverse, shear-action motion components and additionally or alternatively a longitudinal compression wave component.

Although the invention has been described in terms of particular embodiments and applications, one of ordinary skill in the art, in light of this teaching, can generate additional embodiments and modifications without departing from the spirit of or exceeding the scope of the claimed invention. For instance, it is to be noted that multiple transducer assemblies might be used in the same surgical device. Multiple transducers can be electrically driven independently of each other and their combined action would maximize the effectiveness of TRA movement of the surgical tip. Accordingly, it is to be understood that the drawings and descriptions herein are proffered by way of example to facilitate comprehension of the invention and should not be construed to limit the scope thereof.

REFERENCES

Anderson B E, Griffa M, Larmat C, Ulrich T J, and Johnson P A. Time reversal. Acoustics Today 2008, 4, 1: 5-11.

Derode A, Tourin A, Fink M. Time reversal versus phase conjugation in a multiple scattering environment. Ultrasonics 2002, 40 (1-8): 275-280.

Fink M, Time-reversal acoustics, Journal of Physics. 2008; 118, 1-28.

Fink M. Time reversed acoustic, Physics Today. 1997; 3, 34-9.

Sutin A, Libbey B, Kurtenoks V, Fenneman D, Sarvazyan A. Nonlinear detection of land mines using wide bandwidth time-reversal techniques. In: Detection and Remediation Technologies for Mines and Minelike Targets XI: J Thomas Broach, Russell S Harmon, John H. Holloway, Jr; ed. Proc SPIE 6217, 2006; pp. 398-409.

Sutin A and Johnson P. Nonlinear elastic wave NDE II: Nonlinear wave modulation spectroscopy and nonlinear time reversed acoustics. In: Review of Quantitative Nondestructive Evaluation, ed. DO Thompson and DE Chimenti, AIP, New York, 2005; 24, pp. 385-92.

Sutin A and Sarvazyan A. Spatial and temporal concentrating of ultrasound energy in complex systems by single transmitter using time reversal principles. In: Proceedings of World Congress on Ultrasonics Sep. 7-10, 2003; Paris, pp. 863-66.

Sutin A M, Sinelnikov Y D, 2010, Time Reversal Acoustic Approach for Non-Lethal Swimmer Deterrent. Proceedings of the Waterside Security Conference, Marina di Carrara, Italy, November.

Sutin A M and Sinelnikov Y D, 2010, Time Reversal Acoustic Approach for Non-Lethal Swimmer Deterrent, J. Acoust. Soc. Am. Volume 128, Issue 4, pp. 2336-2336, lay-language paper: http://www.acoustics.org/press/160th/sutin.htm.

Quieffin N, Catheline S, Ing R K, Fink M. Real-time focusing using an ultrasonic one channel time-reversal mirror coupled to a solid cavity. J Acoust Soc Am 2004; 115 (5), 1955-60.

Sinelnikov Y D, Vedernikov A V, Sutin A Y, Sarvazyan A P, 2010, Time Reversal Acoustic focusing with a catheter balloon. Ultrasound in Med. & Biol., Vol. 36, No. 1, pp. 86-94, PMID: 19900754.

Sinelnikov Y D, Fjield T, Sapozhnikov O A, 2009, The mechanism of lesion formation by ultrasound ablation catheter for treatment of Atrial Fibrillation. Acoustical Physics Volume 55, 4, 1-12.

What is claimed is:

1. A method for manufacturing a medical instrument, comprising:
fabricating an ultrasonic horn or concentrator having a predetermined shape and size;
operatively connecting an upstream or input portion of said horn or concentrator to an ultrasonic transducer assembly;
energizing said transducer assembly to generate at an input or upstream end of said horn or concentrator an ultrasonic calibration vibration having a desired motion pattern and desired frequency and amplitude characteristics;

automatically tracking movement of an operative tip of said horn or concentrator upon generation of said calibration vibration at said input or upstream end of said horn or concentrator;

automatically recording at least one signal encoding the tracked movement;

processing the recorded signal to generate a time reversal waveform; and storing said time reversal waveform in a storage medium.

2. The method defined in claim 1 wherein said horn or concentrator is a test or calibration device, said transducer assembly being a test or calibration assembly, further comprising packaging said storage medium with an ultrasonic medical instrument including a handle, a horn or concentrator section identical to said test or calibration device and terminating in an operative tip identical to the operative tip of said test or calibration device, a transducer arrangement identical to said test or calibration assembly and disposed in said handle and operatively engaged with said horn or concentrator section for generating ultrasonic mechanical vibrations therein to vibrate said operative tip during contact thereof with target tissue at a surgical site in a patient, and an electrical waveform generator operatively connected to said transducer arrangement for energizing same with an electrical waveform, said waveform generator including said storage medium storing said time reversal waveform.

3. The method defined in claim 1, further comprising packaging said storage medium with an ultrasonic medical instrument including a handle, said horn or concentrator being connected to said handle, said transducer assembly being disposed in said handle and operatively engaged with said horn or concentrator for generating ultrasonic mechanical vibrations therein to vibrate said operative tip during contact thereof with target tissue at a surgical site in a patient, said instrument further including an electrical waveform generator operatively connectable to said transducer assembly for energizing same with an electrical waveform, said waveform generator including said storage medium storing said time reversal waveform.

4. The method defined in claim 1 wherein said ultrasonic calibration vibration is a short pulse, said movement of said tip being a long reverberation signal.

5. The method defined in claim 1 wherein the processing of said recorded signal includes time reversing said recorded signal and normalizing the time-reversed signal.

6. The method defined in claim 1 wherein said transducer assembly is so configured relative to said horn or concentrator to produce, in a proximal end portion of said horn or concentrator, ultrasonic vibrations having a transverse or shear component, said ultrasonic calibration vibration having a transverse or shear component.

7. The method defined in claim 1 wherein said shape of said horn or concentrator is asymmetric about a longitudinal axis of said upstream or input portion of said horn or concentrator.

8. The method defined in claim 1 wherein tracking the movement of said operative tip of said horn or concentrator includes operating at least one laser vibrometer.

* * * * *